United States Patent [19]

Doering

[11] Patent Number: 5,184,217
[45] Date of Patent: Feb. 2, 1993

[54] SYSTEM FOR AUTOMATICALLY INSPECTING A FLAT SHEET PART

[76] Inventor: John W. Doering, 18252 Lincoln St., Villa Park, Calif. 92667

[21] Appl. No.: 562,025

[22] Filed: Aug. 2, 1990

[51] Int. Cl.$^5$ .............................................. H04N 7/18
[52] U.S. Cl. .................... 358/106; 358/101; 382/8; 356/237
[58] Field of Search ........................ 358/106, 101, 107; 382/8; 356/237, 375, 387, 394, 384, 398, 383, 385; 250/560, 561; 359/861, 864, 834, 858, 863

[56] References Cited

U.S. PATENT DOCUMENTS

| | | | |
|---|---|---|---|
| 4,295,198 | 10/1981 | Copeland et al. | 358/101 |
| 4,533,251 | 8/1985 | French et al. | 356/384 |
| 4,555,798 | 11/1985 | Broadbent, Jr. et al. | 358/107 |
| 4,573,798 | 3/1986 | Fujie et al. | 356/380 |
| 4,635,289 | 1/1987 | Doyle et al. | 382/8 |
| 4,692,943 | 9/1989 | Pietzsch et al. | 382/8 |
| 4,711,579 | 12/1987 | Wilkinson | 356/375 |
| 4,751,376 | 6/1988 | Sugiura et al. | 358/497 |
| 4,783,826 | 11/1988 | Koso | 358/106 |
| 4,893,346 | 1/1990 | Bishop | 382/8 |
| 4,978,220 | 12/1990 | Abramovich et al. | 358/101 |

Primary Examiner—James J. Groody
Assistant Examiner—Michael H. Lee

[57] ABSTRACT

An inspection system for automatically documenting and verifying the perimeters and hole dimensions of flat sheet metal workpiece. The system includes an inspection table with a transparent surface upon which the workpiece is placed. A servo controlled rack and pinion gear driven carriage which travels along the table on rails in the X direction. The carriage consists of a shelf above the table containing a fluorescent tube lamp for back illuminating the workpiece, and a shelf below the table surface containing an optical/sensor imaging array module which travels on rails cross the width of the carriage in the Y direction servo driven via a ball screw drive. The optical sensor imaging array is responsive to light energy, detecting light-to-dark and dark-to-light transitions as it scans across the workpiece, the scan transition addresses being representative of the location of the edges of the workpiece. The X and Y axis transition data is processed and stored in a microcomputer for subsequent display, plotting and/or print out.

18 Claims, 6 Drawing Sheets

SYSTEM FOR AUTOMATICALLY INSPECTING A FLAT SHEET PART

BACKGROUND OF THE INVENTION

1. Field of the Invention

This invention relates generally to an automatic high-speed electro-optical inspection system, and more particularly, to a system including an unique inspection table, movable carriage, optical assembly and a light sensitive array which is adapted to automatically scan, verify, measure and document the perimeters and holes formed in a flat sheet metal workpiece.

1. Prior Art

It is common practice to manually inspect punched, flat sheet metal workpieces using scales, calibers, micrometers on other manual instruments. Complex workpieces with complex shapes and/or a multitude of holes becomes laborious, time consuming and highly subject to human error.

Accordingly, automatic electro-optical inspection systems have been developed to increase efficiency, accuracy and reduce the costs of inspection. However, such automatic systems usually involve the X and Y axis movement of the workpiece or light sensor, reading out the coordinate of each edge crossing as it passes by the center of the sensor. Such systems are generally very slow and expensive.

Another example of prior art is a system employing array multiple linear sensors as described in U.S. Pat. No. 4,711,579, dated Dec. 8, 1987 to Blair E. Wilkinson. This system consists of a transparent table surface, with a yoke which moves in one axis along the table. It employs a plurality of linear sensor CCD arrays (five or more), arranged to form a continuous line of optically alinged CCD sensor arrays arranged to electrically scan across the width of the table. Typically each sensor array consists of a single row of 2048 sensor elements. These arrays are mounted onto a yoke which is mechanically moved in one-axis perpendicular to the direction of array scan. The accuracy of this invention is dependent upon the number of CCD sensor arrays employed. In viewing a typical 48 inch wide scanning format a minimum of eight and preferably sixteen overlapping optical sensor arrays would required to approach the accuracies required by the sheet metal industry. The accuracy of this invention is also dependent upon the workpiece being close to a perfect workpiece, i.e. essentially flat, with sharp vertical walled edges and holes. However, the vast majority of sheet metal workpieces in the industry are sheared and punched, resulting in a workpiece that is slightly bowed, with rounded edges and holes due to tool impact and breakout (hole burst and/or burrs). Tool impact imperfections varies with the type of material, material handling and tools applied. Some workpieces are fabricated with countersunk and dimpled holes. The accuracy of the Wilkinson invention can be significantly degraded by these edge variations because of the angular field-of-view inherent in the systems optics. Holes smaller in diameter then the thickness of the workpiece may not be detectable. The transparent glass/plastic table top cannot be maintained in flat horizontal plane over a large area (as it bows towards the center) and the workpiece will typically lie in a plane above or below the plane of scale calibration. This may be compensated for by overlapping the field-of-views so that each edge is viewed by two optical sensor arrays. Such a system is generally expensive, and requires a very precise and difficult to achieve alignment of the sensors and their optics.

Other examples of known systems for inspecting flat sheet metal workpieces are available in one or more of the following U.S. Pat. Nos.:

2,684,009 Jul. 20, 1954
4,319,272 Mar. 9, 1982
4,555,798 Nov. 26, 1985
4,560,273 Dec. 24, 1985

SUMMARY OF THE INVENTION

Briefly, and in general terms, a high performance inspection is disclosed for automatically inspecting, documenting and verifying the position of the dimensions of the perimeters and holes formed in a punched, drilled or laser cut flat sheet metal workpiece. The present system provides an accurate, high speed and cost effective improvement over the time consuming and error prone techniques which have heretofore been used for inspecting flat workpieces.

The present system comprises an transparent glass topped inspection table upon which a workpiece is placed. A rack and pinion gear driven carriage is mounted on rails, and servo driven in the X direction across the length of the table. The carriage includes oppositely aligned horizontal top and bottom shelves, the top shelf supporting an apertured fluorescent lamp which illuminates the table surface in a line in the Y-direction across the width of the table. The bottom shelf contains an optical sensor module which is mounted on rails, and servo driven for positioning in the Y direction. Electrical mechanical X and Y axis positioning are read-out by two phase rotary optical encoders.

The optical sensor module consists of a single two-dimensional charged coupled device (CCD) imaging sensor with an optical system consisting of a lens, two flat mirrors and a curved mirror. The mirrors provide for the folding of optical path to minimize the length of the optical sensor module and to enhance the use of a long focal length lens. The curved mirror is curved into two axes (and Y-directions) to bend the light path so that each element of the two-dimentional sensor array is viewing the workpiece from a vertical angle, essentially eliminating the effects of edge imperfections (tool impact), countersunk or dimpled holes, and variations in workpiece thickness.

The CCD sensor is a time delay and integration (TDI) two dimensional area array imaging sensor. It is clocked and synchronized to match the rate of carriage movement in the X-direction. The analog video outputs from the sensor are processed into a serial 1-bit digital video signal, with logic transitions corresponding to edge changes as the sensor scans the workpiece.

The sensor and its optics are aligned and calibrated by scanning a precision glass scale located in the surface at one end of the table. The optical sensor module is programmed to scan the surface of the table in the X-direction in twelve scan passes, each overlapping the proceeding scan by one percent.

The digital video, clock, and blanking and signals from the optical sensor module are fed into a edge Data Processor Circuit Board, which mounts into a plug-in circuit board slot in a standard personal computer. The edge Data Processor processes the digital video data into white-to-black and black-to-white edge transition position counts (run-length count) which is entered into a first-in-first-out (FIFO) memory.

The position of the carriage in the X-direction and the optical/sensor module in the Y-direction are readout by optical encoders, each of which drives a counter on in the Video Data Processor. The Y-count is latched at the end of each sensor line scan and entered into the first-in-first-out (FIFO) memory. The end of scan signal sets a computer interrupt, and the edge, carriage and module position data is read out of the FIFO by the computer and entered into computer memory for software processing. At the beginning of each scan pass, on computer command, the X-axis position of the optical sensor module is readout by the computer. The sensor picture element (pixel) data edge transition counts and X and Y-axis sensor position counts determine the address location of points on the perimeter and hole edges of the workpiece. The resulting data is software processed for scaling, measurement and comparison computations, display, printout and plotting.

DESCRIPTION OF THE DRAWINGS

Preferred exemplary embodiments of the present invention will hereinafter be described in conjunction with the appended drawings wherein like designations denote like elements, and.

DESCRIPTION OF THE PREFERED EMBODIMENT

Figure 1:
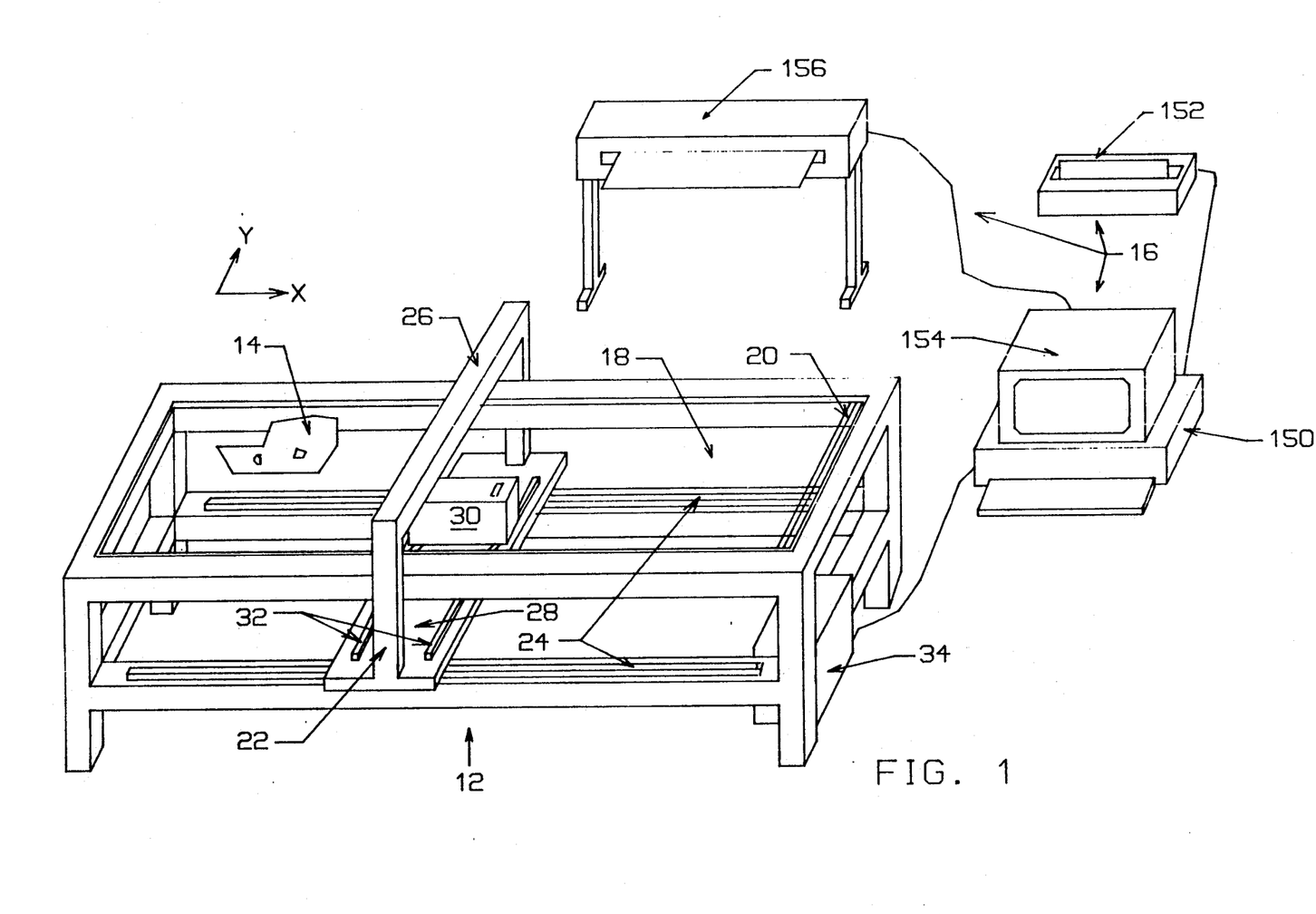
FIG. 1 is perspective view showing the automatic inspection system, which forms the present invention.

In automatic inspection system of the present invention for sensing and measuring the position of the perimeters and the location and dimensions of holes in a metal workpiece are best described while referring to the drawings. In FIG. 1, there is an inspection table 12 upon which a workpiece 14 is placed. The inspection table and computer workstation 16 functions as the mounting points for all of the soon-to-be-described components of the system. By way of example only, the inspection table is fabricated from steel. The table can be configured in a variety of sizes, for scanning workpieces up to 48-inches by 94-inches. The table has a typical working height of 28-inches, and an overall height of 36-inches.

The top of the table contains an optically quality transparent flat sheet (0.375-inch thick) of plastic laminated high strength safety glass 18, chemically hardened to resist abrasion and scratching. A precision calibration scale 20, consisting of a pattern of graduated markings etched in black on a transparent optical quality flat glass plate is located at one end of the table. It is used to optical align, and automatically calibrate (scale) the sensor in the Y-axis direction.

The table includes a carriage 22 which is mounted on precision rails 24, and positioned in the X-axis direction by a dc motor via a rack and pinion gear interface. The carriage has two shelves, the upper shelf 26 containing a fluorescent lamp which illuminates the top of the table surface, and the bottom shelf 28 containing an optical sensor module 30 which views the bottom of the table surface. The optical sensor module is mounted on rails 32 on the bottom shelf and positioned in the Y-axis direction by a dc motor via a pre-loaded ball screw drive.

Upon applying power, the optical sensor module 30 and the carriage 22 are driven to a home end position at one corner of the table (established by limit switches) which serves as the referenced origin for movement in the X-axis direction (first direction) and Y-axis direction (second direction). The carriage 22 scans down the length of the table in the X-axis direction, and as it returns the optical sensor module 30 is incremented to an adjacent position so that its field-of-view overlaps the previous scan by about one percent; the carriage 22 repeats its scan pass down the table; repeating until the table top area has been scanned. If the workpiece 14 is placed near the home position, the system can be software setup to scan only the workpiece 14, or a predetermined area of the table to reduce scanning time.

Figure 2:
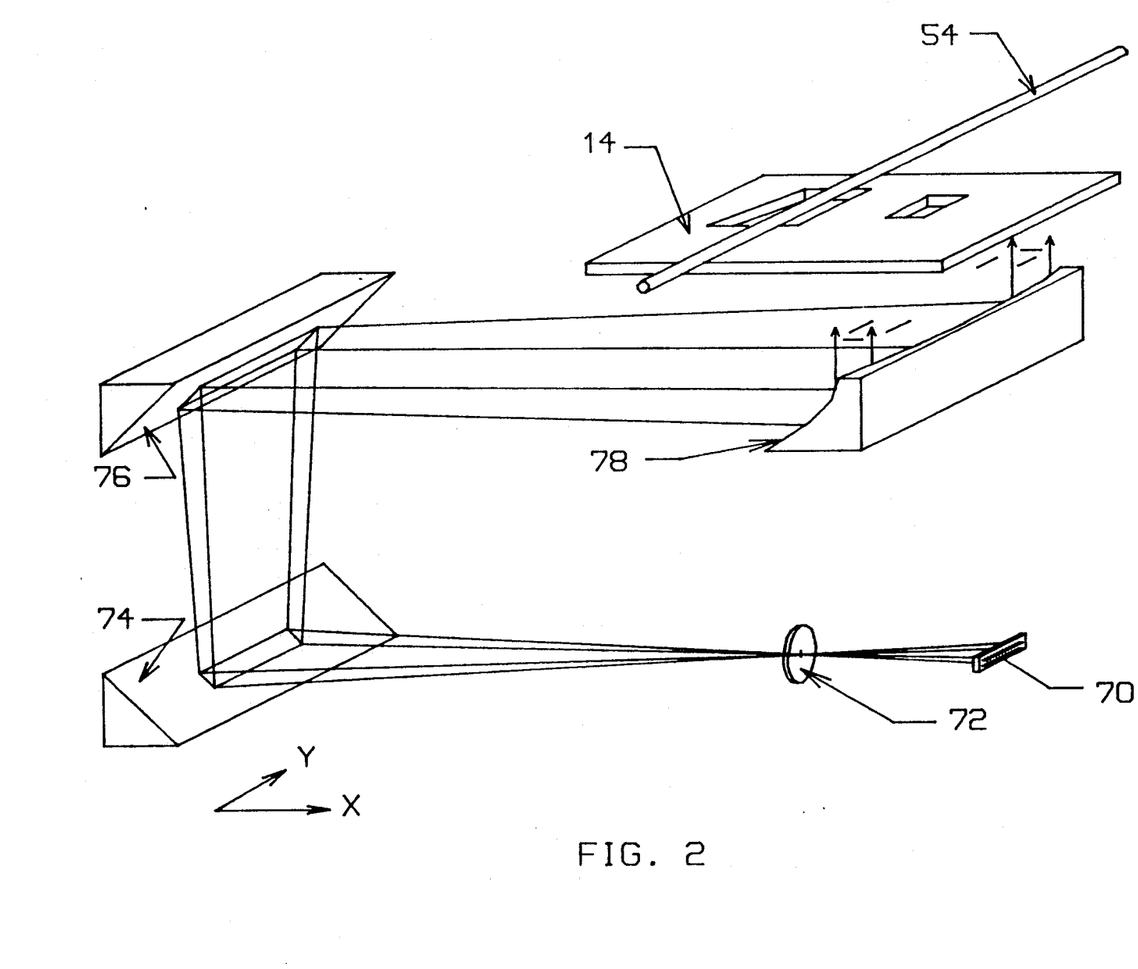
FIG. 2 is a perspective diagram describing the functional configuration of the optical/sensor module sub-system.

Carriage 22 and optical sensor module 30 motion control positioning, are closed loop servo sub-systems, controlled by the microcomputer 150, via a two axis (X-axis and Y-axis) motion controller 40 (FIG. 2), which is located within a power/control sub-system enclosure 34 on the side of the table. The X-axis output is buffered through X-axis servo amplifier 46, to a dc gearhead motor 42, to position the carriage 22 via a pinion gear and gear rack drive mechanism 58. The Servo position/rate feedback data for carriage 22 (of FIG. 1) travel (X-axis) is generated by a rack and pinion geared two-phase rotary optical encoder 50 (FIG. 2). The Y-axis output is buffered through Y-axis servo amplifier 62 to position the optical/sensor module 30 via a pre-loaded ball screw drive mechanism 60. Servo position/rate feedback data for optical sensor module 30 travel (Y-axis) is generated by a two-phase rotary optical encoder 52 coupled to the ball screw drive. The motion position controller 40 is setup (software programmed) and controlled via a standard RS232 serial port interface with the system's microcomputer 150 (FIG. 2).

A very high output apertured fluorescent lamp 54 (FIG. 2) on the upper shelf 26 (of FIG. 1) illuminates the top of the table and the workpiece 14. The lamp is driven by a regulated high frequency ballast power supply 56 (FIG. 2) to minimize flickering and noise, and to maintain a relatively constant level of high intensity illumination. The lamp is mounted so as to always be in opposite alignment with the optical port of the optical/sensor module 30.

Figure 3:
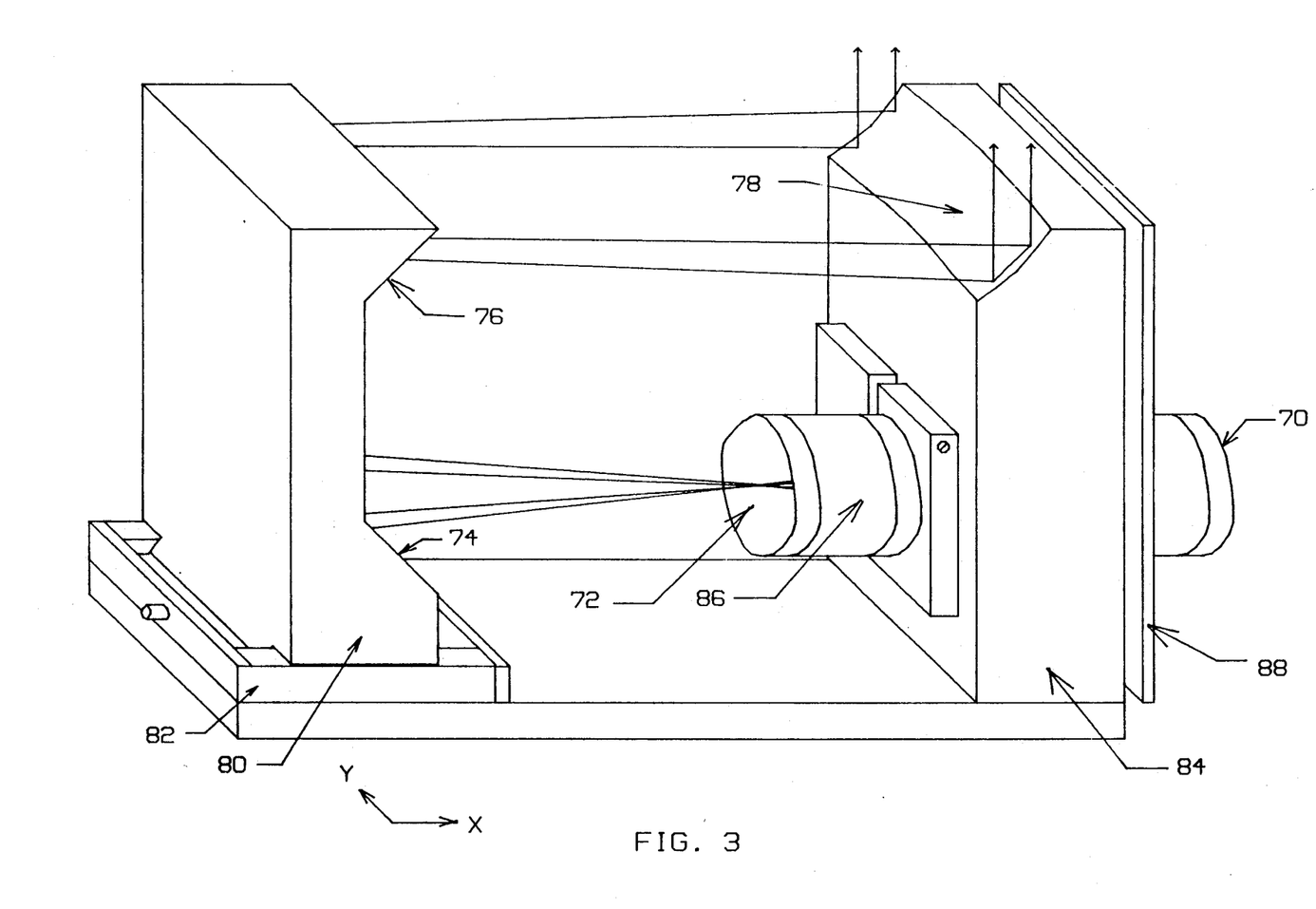
FIG. 3 is a perspective view of the optical/sensor module sub-system showing the mechanical components.
Figure 4:
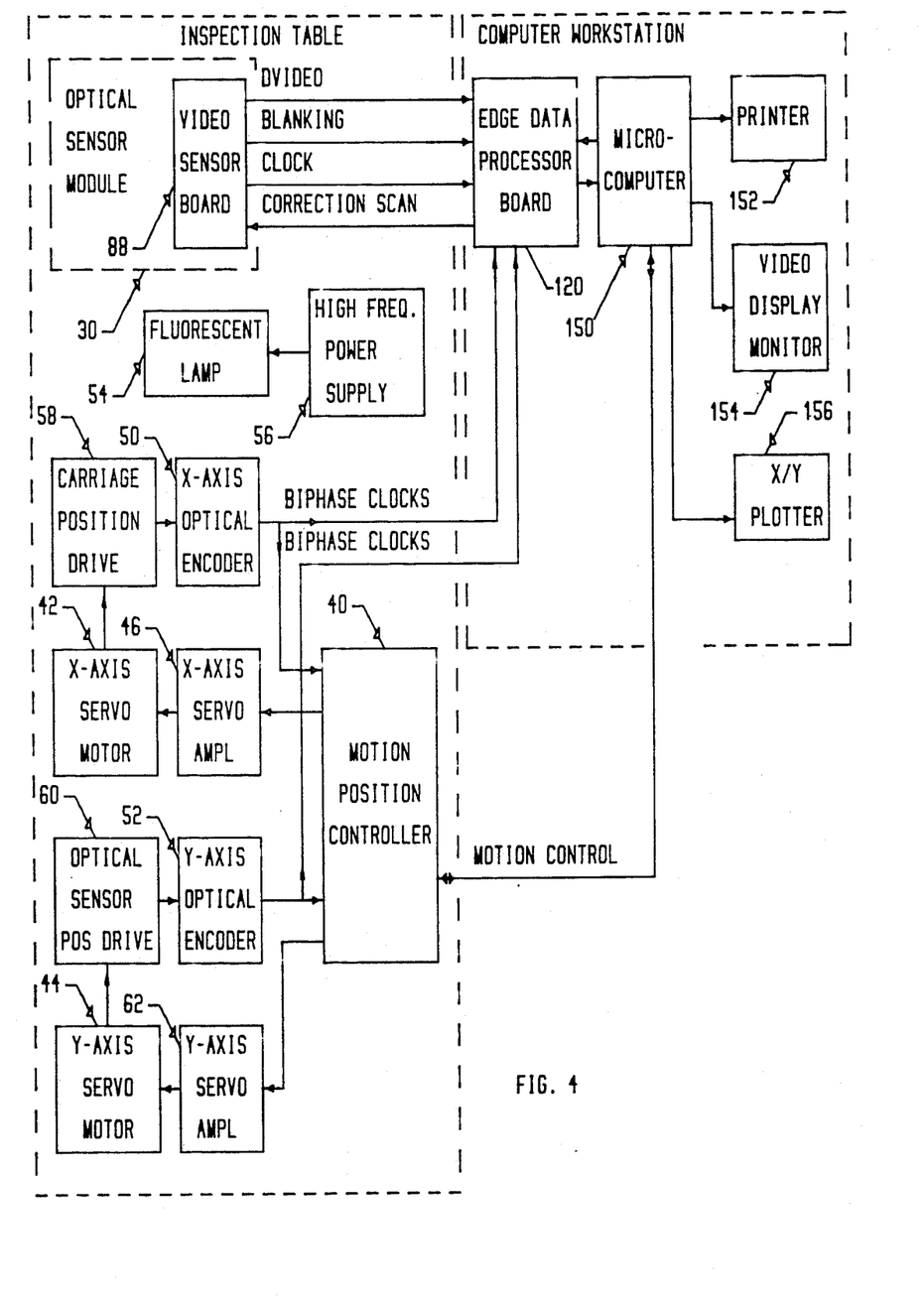
FIG. 4 is an overall functional block diagram of the inspection system's electronics which forms the present invention.

The optical system described by FIG. 3 and FIG. 4 consists of a Charge Coupled Device (CCD) imaging sensor array 70, a 135 millimeter focal length enlarging lens 72 (FIG. 3) with an aperture of f#22 or f#32, two flat mirrors 74 and 76 and one curved mirror 78. The optics are aligned and positioned so that the array is in focus to view the workpiece 14 at and above the transparent surface of the table, which is illuminated by the apertured fluorescent lamp 54. The curved mirror 78 is a spherical segment, curved at radius which bends the light rays so that each element of the sensor is viewing perpendicular to the table. The two mirrors 74 and 76 (FIG. 4) are mounted onto the mirror assembly 80 which is mounted on a micro-positioned slide 82 to provide for optimum setup of the sensor-to-table surface distance. The curved mirror 78 and the lens/sensor assembly 85 are mounted the optical assembly 84. The optical assembly 84 consists of a machined mounting for the lens 72, CCD imaging sensor 70, and adjustable lens extender 86, and the video sensor board 80. The optical assembly 84 provides for the setup of the lens-to-sensor spacing and rotation alignment. Prior to installation into the carriage 22 (FIG. 1), the relative mechanical positioning of the sensor 70, lens 72 and mirrors 74, 76 and 78 are precisely setup on an optical bench for the desired field of view and focus at the table surface. The system is typically setup for a achieving a ±0.001-inch measurement resolution with greater than a 0.5-inch depth of focus.

Figure 5:
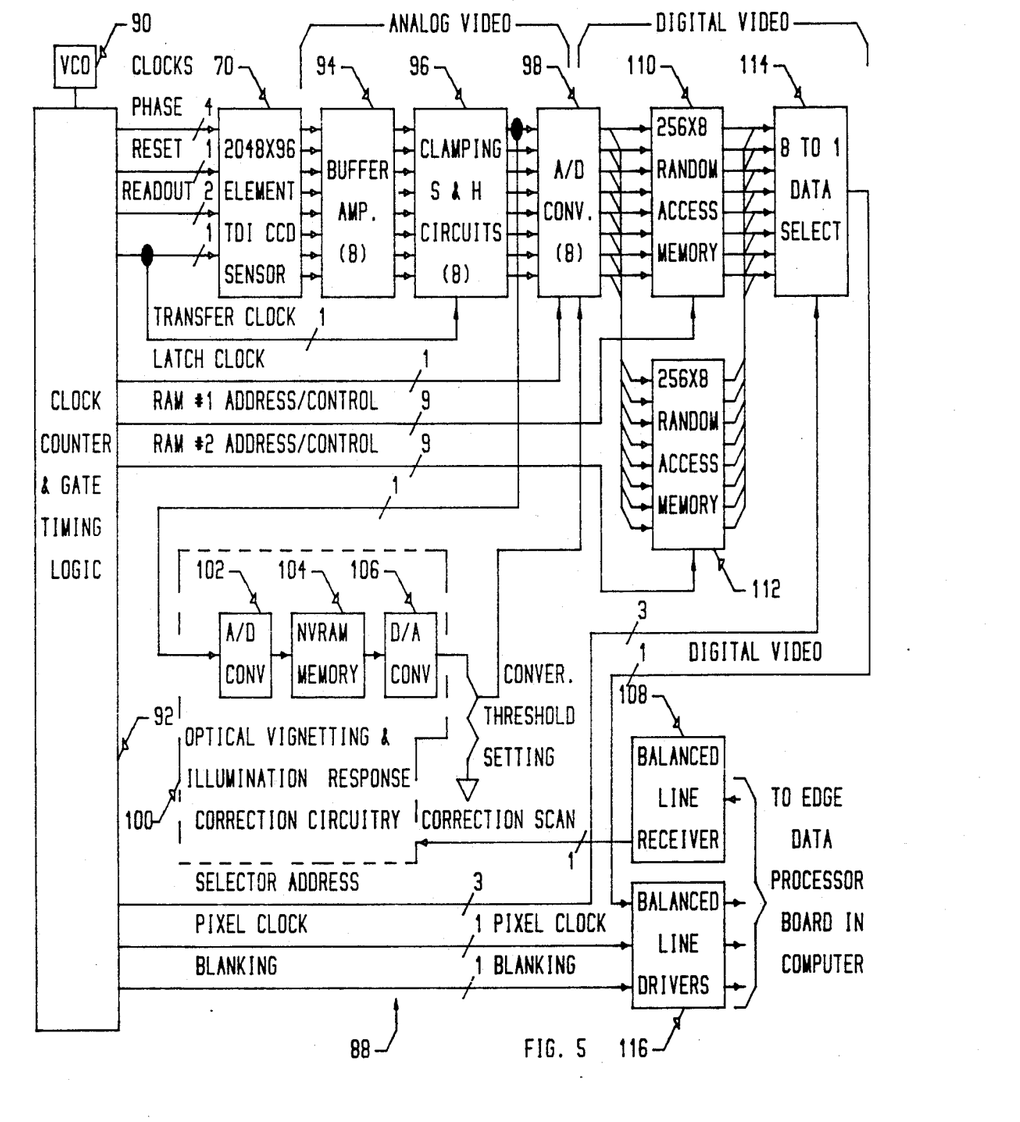
FIG. 5 is a functional block diagram of the video sensor data processing electronics in the optical/sensor module.

FIG. 2 describes an overview of the electronic components of the system. The optical sensor module 30 contains the CCD imaging sensor 70 and the video sensor board 88 which are described in detail in FIG. 5. Referring to FIG. 5, the CCD imaging sensor 70 is a time delay and integration (TDI) two dimensional area array imaging sensor, which provides for a ninety-six times greater sensitivity than a single line linear array sensor. The CCD imaging sensor 70 consists of 96 rows (X-axis) of 2028 photo sensitive elements (Y-axis) configured into a Time Delay Integration (TDI) mode of operation. By way of example, a suitable CCD sensor for use herein is the Type IT-E1-2048 Two Dimensional Sensor manufactured by Dalsa, Inc. Waterloo, Ontario, Canada.

The CCD imaging sensor is aligned so that the 2048 CCD element rows are aligned in the Y-axis direction. As the sensor is moved to scan the table surface in the X-axis direction, the charge (image data) accumulated in each row of 2048 elements is transferred in parallel in the X-axis direction from row to row, in a scrolling format, to a 2048 element output shift register, with eight output taps. The four phase imager, readout and transfer clocks are synchronized with carriage motion in the X-axis, so that the image is moving across the imager plane at the same rate as the signal charge is being transferred from row-to-row.

The video sensor board 88 (FIG. 2) contains a crystal oscillator clock 90, counter and gate circuitry 92 which generates the required clocks, transfer and synchronizing signals for driving the 2048 by 96 element TDI CCD array sensor 70. The CCD array sensor data output consists an analog delay line with eight analog video output taps of 256 picture elements (pixels). Each of the eight analog outputs from the array are buffered through buffer amplifiers 94, dc clamped and deglitched by a clamping sample and hold circuit 96, and processed through an analog to digital converter 98 (a precision comparator) for conversion into a 1-bit digital video format.

Optical vignetting and illumination response correction circuitry 100 provides automatic compensation for optical vignetting and variations in illumination levels across the table in the Y-axis direction. The circuit consists of an analog-to-digital converter 102, a 4096 by 8 bit non-volatile random access memory 104, and an eight-bit (256 grey levels) digital-to-analog converter 106. The correction is achieved by scanning a clean clear area of the table and storing the amplitude (light level) response for every eighth sensor pixel in random access memory for a line of scan across the table. The clear scan amplitude data is readout from memory, converted into an analog signal and applied at half amplitude (adjustable) as an input to each of the eight analog-to-digital converters (comparators) for comparison with the analog video signal input for optimum conversion into a 1-bit digital video format. The command to perform a correction scan is periodically generated, by operator command, via his keyboard interface with the microcomputer 150, the signal being received via a balanced line receiver 108.

The eight digital video outputs from the analog-to-digital converters 98 are interfaced into two alternating random access memories (RAMs) 110 and 112 each with a capacity of 256 by 8 bits. One RAM records a line of scanned digital video data from the imaging sensor, while the proceeding line of scanned data is being readout from the other RAM, through an eight input to one output data selector 114, into a single serial digital video signal format. Pixel clock, blanking and digital video signals are interfaced into the edge data processor board 120 (FIG. 6) via balanced line drivers 116.

Figure 6:
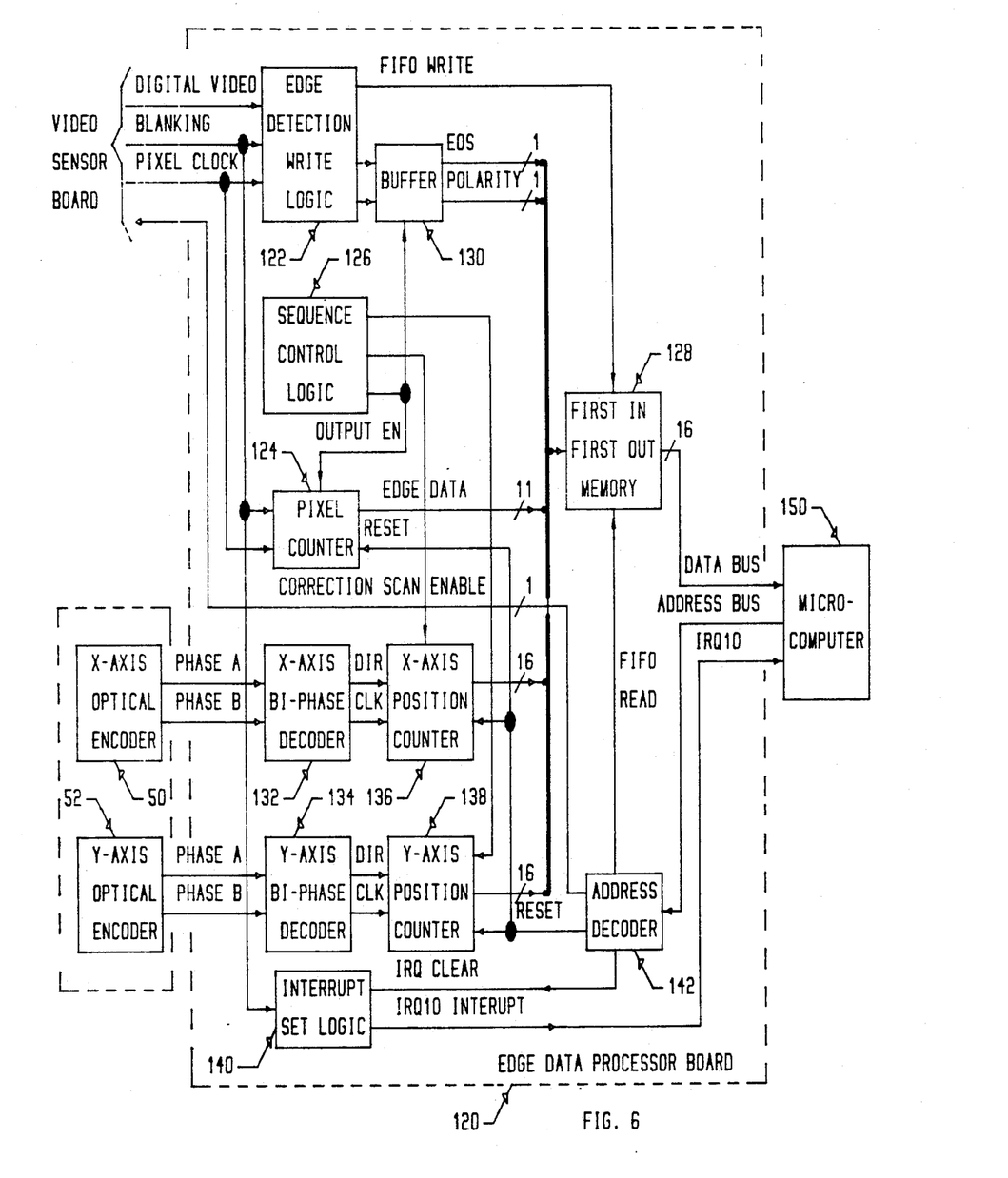
FIG. 6 is a functional block diagram of the edge data processing electronic in the microcomputer.

The edge data processor board 120 (FIG. 2 and 6) is a circuit board which mounts into a standard IBM AT or compatible AT 80386 or AT 80486 Personal Microcomputer 150. It interfaces between the video sensor board 88 (FIG. 5), X and Y axis two-phase optical encoders 50 and 52 (FIG. 2), and the microcomputer's 150 data bus. Referring to FIG. 6, the synchronizing blanking and clock signals are interfaced with a pixel counter 124, the output of which corresponds to pixel addresses of the video data scanned by the CCD sensor in the Y axis. The pixel counter 124 output interfaces into a first-in-first-out (FIFO) memory 128. The digital video signal is clocked through edge detection flip-flop logic 122 which generate a "FIFO write" pulse whenever the digital video signal changes direction (crosses an edge). The "FIFO write" pulse causes the edge address and video polarity (change to white or to black) to be written into the FIFO memory 128. The sequence control logic 126 and TS buffer 130 controls the sequence of data entry into the FIFO. The outputs from X and Y axis optical encoders 50 and 52 are each decoded by bi-phase decoders 132 and 134, and interfaced with up/down address position counters 136 and 138. At the end of each CCD sensor line scan, the X-axis address position of the carriage and the Y-axis position of the optical sensor module from counters 136 and 138 are entered into the FIFO 128, and an interrupt signal from interrupt set logic 120 is sent to the microcomputer 150. The microcomputer 150 responds, via the address decoder 142, by clearing the interrupt and clocking out the FIFO memory 128 buffered pixel edge, and X-axis and Y-axis position address data into computer memory (disk and RAM memory). The Computer workstation is comprised of a microcomputer and peripheral components for data display and hardcopy print out. The microcomputer 150 is a commercially available high speed personal computer, IBM or compatible AT type, configured with a high capacity virtual RAM disk, high capacity hard disk drive, and a floating point array processor board for high speed data manipulation and computation. Software provides for control of carriage motion, and for the computation and processing of data for display on the video display monitor 154, printout via the printer 152 and/or the X/Y plotter 156. The software can be configured to provide for reverse engineering for generating a dimensional drawing of the workpiece 14 (FIG. 1), for duplicating the workpiece, or for comparison of the workpiece with a master part or file.

By virtue of the present invention, an economical high speed, highly accurate inspection system is available for documenting and verify on a CRT screen, graphic printer, column printer and/or X/Y plotter, the perimeter and hole dimensions of a flat workpiece. The present system is a fully automatic and non-contact measurement system, requiring no operator setup time thereby providing a significant savings of time compared with the traditional and time consuming approach of physical contact measurements using calibers, gages, tape measure and/or X/Y coordinate mechanizations. It can accurately measure sheared, punched, drilled and laser cut workpieces with rounded edges, and countersunk and dimpled holes. It establishes a measurement grid of five hundred pixels per inch in both axes, i.e. a measurement accuracy of ±0.001-inch. Unlike many of these systems, the workpiece remains stationary and only the carriage is moved in the X-axis direction and the optical/sensor array module is moved in the Y-axis direction. This avoids the relatively complex prior art inspection process of rotating and/or moving the workpiece in two directions manually or by motors. The present system utilizes an optical design that provides for a non-contact vertical (perpendicular) optical alignment of the elements of a single sensor imaging CCD array in viewing a typical workpiece, thereby providing a significant improvement in accuracy over non-contact systems employing a plurality of linear array sensors in a non-perpendicular optical viewing alignment.

It will be apparent that while a preferred embodiment of the invention has been presented for the purpose of illustration and description. It is not intended to be exhaustive or to limit the invention to the precise form disclosed. Many modifications and variations are possible in light of the above teaching. It is intended that the scope of the invention be limited not by this detail description, but rather by the claims appended hereto. For example, although the present inspection system has been described with reference to the perimeter and holes in a flat sheet metal workpiece, it is to be understood the present system has application for documenting and verifying the perimeter and holes made in any opaque or semi-opaque workpiece regardless of composition. It is also to be understood that the present system can be configured without departing from the true spirit and scope of the invention with other open-loop and closed loop motion control positioning drives; and/or with three flat surfaced mirrors with a scanning pattern setup so that each sensor scan overlaps the previous scan by more than fifty percent.

Having set forth a preferred embodiment of the present invention, what is claimed is:

1. A system for automatically inspecting a workpiece for the perimeter and holes formed therein, said system comprising of:
   an inspection table having a transparent scratch resistant glass surface upon which the workpiece is to be laid;
   an etched glass calibration scale located at the edge of the glass surface of the table for sensor table calibration;
   a carriage mounted on rails on the table which is movable in a first direction; containing a light source, and an optical sensor module which is movable in a second direction perpendicular to the first;
   an imaging sensor with a plurality of photo sensing elements, a lens, two flat mirrors and a curved mirror situated within said optical sensor module;
   a video sensor board situated with said optical sensor module;
   a computer controlled two axis motion controller for controlling the positioning of the carriage in one direction and the optical sensor module in a second direction perpendicular to the first; and
   a computer workstation interfacing with the motion controller, imaging sensor and video sensor board; providing the means for carriage motion control, and the processing of edge address data for workpiece perimeter and hole inspection;
   wherein the curved mirror is a spherical section curved at a radius which aligns the viewing angle of each photo sensing element of the sensor so that it is perpendicular to and focused at the surface of the transparent table top.

2. The inspection system recited in claim 1, wherein the carriage is mounted on rails and movable in the first direction, by a motor driven mechanical drive with optical encoder position feedback, controlled by the motion controller in a closed loop servo configuration.

3. The carriage recited in claim 2, wherein the carriage is comprised of an upper shelf containing an apertured fluorescent lamp illuminating the top surface of the table and the workpiece; and a lower shelf with an optical sensor module mounted onto rails and movable in the second direction by motor mechanical driven drive with an optical encoder feedback, controlled by the motion controller in a closed loop servo configuration.

4. The carriage recited in claim 3, wherein the fluorescent lamp is positioned above the transparent glass table surface in an opposing alignment with the optical sensor module below the surface, illuminating the optical port of the optical sensor module around the perimeters and through holes of the workpiece over its travel in the second direction.

5. The inspection systems recited in claim 1, wherein the imaging sensor contained with the image sensor module is a time delay integration charged coupled device; comprised of a plurality of rows and columns of photo sensing elements, with the rows aligned perpendicular to the first direction; wherein the motion of the carriage in the first direction is synchronized with the scanning of the imaging sensor so that as the image passes each row of sensor elements, the signal charge generated in the sensor is passed from one row to the next row, with the signals being summed over the plurality of rows before being transferred to a readout shift register; and providing an indication of the location of the edges of the perimeter and holes in the workpiece, relative to the location of the optical sensor and its photo sensing elements as it scans the workpiece on the table surface.

6. The inspection system recited in claim 1, wherein the optical sensor module is configured in an optical arrangement comprised of the sensor, an enlarging lens and mirrored surfaces; with the mirror(s) arranged to fold the optical path to achieve a compact module, with the furthest mirror from the sensor being curved.

7. The inspection system recited in claim 1, wherein the video sensor board is comprised of the circuitry for timing and synchronization; analog video signal clamping, sample-and-hold de-glitching; optical vignetting and illumination variation correction, analog to digital video conversion, memory buffering; and interfacing with the sensor and edge data processor board.

8. The inspection system recited in claim 1, wherein the computer workstation is comprised of a computer for data interfacing, processing and storage; plug-in circuit board slots; and software for data manipulation, measurement and comparison computations; and computer peripherals for data display and plotting.

9. The inspection system recited in claim 1, wherein the edge data processor board plugs into the computer and is comprised of circuitry for interfacing with the clock, timing and digital video signals from the video sensor board, bi-phase signals from the X and Y-axis optical encoders; and computer address and data buses; circuitry for pixel address counting, X and Y axis optical sensor position counting, and writing edge addresses into a first-in-first-out memory for buffering edge address data onto the computer data bus.

10. A system for automatically inspecting a workpiece for the perimeter and holes formed therein, said system comprising:
an inspection table having a transparent glass surface upon which the workpiece is to be laid;
an etched glass calibration scale located in the plane of the glass surface of the table for sensor scale calibration;
a carriage mounted on rails on the table which is movable in a first direction; containing a light source, and an optical sensor module which is movable in a second direction perpendicular to the first;
an imaging sensor with a plurality of photo sensing elements, a lens, and a curved mirror situated within said optical sensor module;
a video sensor board situated with said optical sensor module;
a computer controlled two axis motion controller for controlling the movement of the carriage in one direction and the optical sensor module an a second direction perpendicular to the first; and
a computer workstation interfacing with the motion controller, imaging sensor and video sensor board; providing the means for carriage motion control, and the processing of edge address data for workpiece perimeter and hole inspection;
wherein the curved mirror is curved to align the viewing angle of each photo sensing element of the sensor so that it is perpendicular to and focused at the surface of the transparent table top.

11. The inspection system recited in claim 10, wherein the carriage is mounted on rails and movable in the first direction, by a motor driven mechanical drive controlled by the motion controller.

12. The carriage recited in claim 11, further comprising of an upper shelf containing a fluorescent lamp illuminating the top surface of the table and the workpiece; and a lower shelf with an optical sensor module mounted onto rails and movable in the second direction by motor mechanical driven drive controlled by the motion controller.

13. The carriage recited in claim 10, wherein the fluorescent lamp is positioned above the transparent glass table surface in an opposing alignment with the optical sensor module below the surface, illuminating the optical port of the optical sensor module through the workpiece over its travel in the second direction.

14. The inspection system recited in claim 10, wherein the imaging sensor contained within the optical sensor module is a time delay integration charged coupled device; comprising of a plurality of rows and columns of photo sensing elements, with the rows aligned perpendicular to the first direction; wherein the motion of the carriage in the first direction is synchronized with the scanning of the imaging sensor so that as the image passes each row of sensor elements, the signal charge generated in the sensor is passed from one row to the next row, with the signals being summed over the plurality of rows before being transferred to a readout shift register; and providing an indication of the location of the edges of the perimeter and holes in the workpiece, relative to the location of the optical sensor and its photo sensing elements as it scans the workpiece on the table surface.

15. The inspection system recited in claim 10, wherein the optical sensor module is comprised of the photo sensor, an enlarging lens and curved mirror; arranged to fold the optical path to achieve a compact module.

16. The inspection system recited in claim 10, wherein the video sensor board is comprised of the circuitry for timing and synchronization; analog video signal clamping, sample-and-hold de-glitching; analog to digital video conversion, memory buffering; and interfacing with the sensor and edge data processor board.

17. The inspection system recited in claim 10, wherein the computer workstation comprising of a computer for data interfacing, processing and storage; plug-in circuit board slots; and software for data manipulation, measurement and comparison computations; and computer peripherals for data display and plotting.

18. The inspection system recited in claim 10, wherein the edge data processor board plugs into the computer and is comprised of circuitry for interfacing with the clock, timing and digital video signals from the video sensor board; and computer address and data buses; circuitry for pixel address counting, and writing edge addresses into a first-in-first-out memory for buffering edge address data onto the computer data bus.

* * * * *